United States Patent [19]

Espitalie et al.

[11] Patent Number: 4,519,983
[45] Date of Patent: May 28, 1985

[54] METHOD AND DEVICE FOR DETERMINING THE ORGANIC CARBON CONTENT OF A SAMPLE

[75] Inventors: Jean Espitalie, Le Vesinet; Marcel Madec, Suresnes, both of France; Paul Leplat, Leuven; Jacques Paulet, Emines, both of Belgium

[73] Assignees: Institut Francais du Petrole, Rueil-Malmaison, France; Société Labofina S.A., Brussels, Belgium

[21] Appl. No.: 401,595

[22] Filed: Jul. 26, 1982

Related U.S. Application Data

[62] Division of Ser. No. 219,616, Dec. 24, 1980, Pat. No. 4,352,673.

[30] Foreign Application Priority Data

Dec. 28, 1979 [FR] France .................................. 79 32019

[51] Int. Cl.$^3$ ............................................ G01N 31/12
[52] U.S. Cl. .......................................... 422/78; 422/80; 422/89; 422/93; 436/145; 436/155; 436/157; 436/160
[58] Field of Search ............... 422/68, 54, 78, 89, 422/79, 93, 80, 158; 436/145, 146, 155, 157, 158, 160, 138, 115, 152, 159

[56] References Cited

U.S. PATENT DOCUMENTS

| | | | |
|---|---|---|---|
| 2,427,261 | 9/1947 | Crawford | 422/83 |
| 3,861,874 | 1/1975 | Krc | 436/157 X |
| 3,953,171 | 4/1976 | Espitalie et al. | 436/32 |
| 3,954,408 | 5/1976 | Dugger | 436/159 X |
| 4,040,789 | 8/1977 | Voss et al. | 436/181 X |
| 4,098,576 | 7/1978 | Judge | 436/75 |
| 4,213,763 | 7/1980 | Madec et al. | 436/160 X |
| 4,229,181 | 10/1980 | Espitalie et al. | 436/155 X |

Primary Examiner—Barry S. Richman
Assistant Examiner—Michael S. Gzybowski
Attorney, Agent, or Firm—Millen & White

[57] ABSTRACT

A method and apparatus for determining the total amount of organic carbon in a sample comprising the successive steps of: (a) heating the sample in an inert atmosphere to a first temperature capable of cracking at least a fraction of the organic material contained in the sample; (b) measuring the amount of organic carbon contained in at least a fraction of the effluent resulting from this cracking; (c) heating the sample in an oxidizing atmosphere to a second temperature at most equal to the first temperature; (d) measuring the amount of organic carbon in the effluent produced by the oxidation of the organic material, and (e) deriving from the above measurements the total organic carbon content of the sample. In order to perform the method of the invention, there is also provided means for performing each of the successive steps. In a further refinement, the method also includes steps for determining the mineral carbon content so that the total carbon content of the sample can be determined.

8 Claims, 3 Drawing Figures

METHOD AND DEVICE FOR DETERMINING THE ORGANIC CARBON CONTENT OF A SAMPLE

This is a division of application Ser. No. 219,616 of Jean Epistalie et al., filed Dec. 24, 1980, now U.S. Pat. No. 4,352,673.

BACKGROUND OF THE INVENTION

The present invention relates to a method and a device for determining, in particular, the amount of organic carbon contained in a sample, this method also permits, if necessary, the determination of the mineral carbon content.

Various methods are already known for determining the quantity of carbon contained in liquid samples.

One of these methods, of which some embodiments are described in FRENCH PATENT Application No. 2,265,095 and in U.S. Pat. Nos. 3,296,435 and 3,530,292 consists of oxidizing a sample at a high temperature and measuring the amount of carbon dioxide which is obtained, this amount representing the total quantity of carbon contained in the sample. However, this method does not permit distinguishing between the mineral and the organic carbon in the sample.

According to another method of analyzing a liquid sample, which is described in U.S. Pat. No. 3,607,071 and BRITISH Pat. No. 1,494,906, the sample is subjected to a preliminary treatment to extract the mineral carbon therefrom.

A subsequent oxidation of the remaining fraction of the sample and the measurement of the amount of carbon dioxide so obtained permits determination of the amount of organic carbon. However, this method is time-consuming.

According to another method described in FRENCH PATENT Application No. 2,420,141 and in U.S. Pat. No. 3,672,841, the total amount of carbon contained in a sample is determined by heating the latter in an oxidizing atmosphere to at least 1000° C., and measuring the amount of carbon dioxide produced during this heating step. It is assumed that by subjecting a second sample to a similar treatment at a temperature which does not exceed 600° the measurement of the amount of the carbon dioxide so-produced represents the amount of organic carbon in the sample. The difference between these two results gives the amount of mineral carbon.

In practice, if the first measurement is actually representative of the total amount of carbon contained in the sample, the measurement performed on the second sample can only be valid if the sample contains no carbonate, since carbonates are decomposed under 600° C., of if the carbonate amount is small compared to the amount of organic carbon. In other words, the accuracy in the determination of the amount of organic carbon is not known and the same occurs for the amount of mineral carbon which is derived from the difference between the value of the total carbon amount and the value of the amount of organic carbon.

The method for determining the organic carbon content in a geological sample which is described in BELGIAN Pat. No. 852,335 consists of pyrolyzing a sample in an inert atmosphere, measuring the amount of so-obtained benzene and deriving from this measurement, on the basis of a pre-established chart, the amount of organic carbon contained in the sample. The difficulty of this method lies in the necessity of pre-establishing a chart, and moreover, the accuracy of the results obtained by this method is low.

It is already known from FRENCH PATENT application No. 2,376,414 to pyrolyze a sample in an inert atmosphere so as to measure the sulphur compounds after oxidation of the pyrolysis products.

However this method cannot be applied to the determination of the amount of organic carbon contained in a sample of geological sediment.

With respect to these methods, the object of the present invention is to permit a faster and more accurate determination of the respective amounts of organic and mineral carbon, these results being obtained from a single sample.

BRIEF DESCRIPTION OF THE DRAWINGS

The invention will be readily understood and all its advantages will become clearly apparent from the following description illustrated by the accompanying drawings wherein.

DETAILED DISCUSSION OF THE INVENTION

Figure 1:
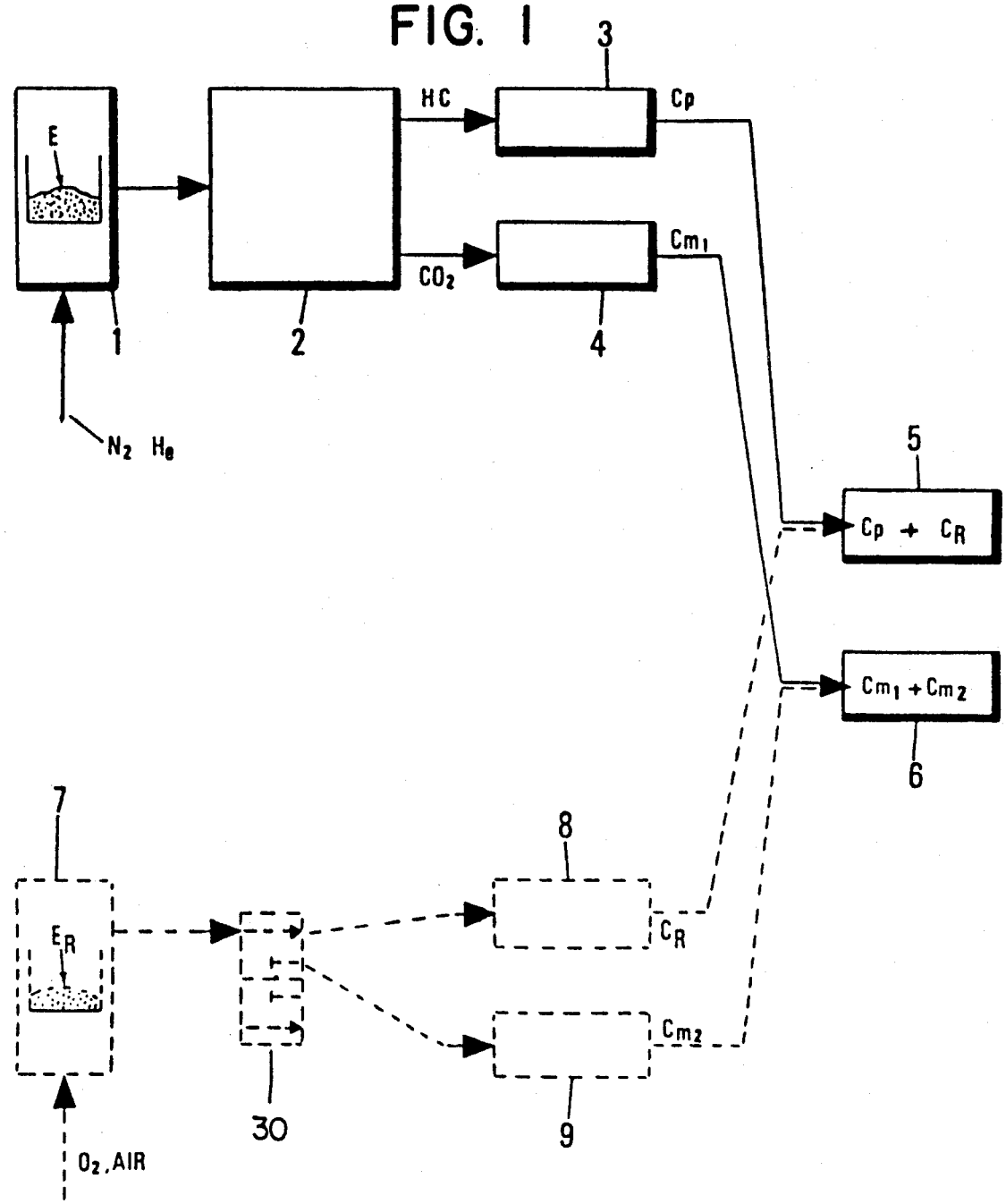
FIG. 1 diagramatically illustrates the method according to the invention.

The process according to the invention, diagrammatically illustrated in FIG. 1, comprises pyrolyzing the sample E in a first heating chamber 1 in an inert atmosphere and at a temperature $\theta_1$ comprised between 500° and 600° C., this pyrolysis producing a cracking of the organic material contained in the sample.

The effluents resulting from this pyrolysis are analyzed in 2 so as to determine, on the one hand, the amount of hydrocarbon products (H-C) and, on the other hand, the amount of carbon dioxide ($CO_2$) produced by the early decomposition of some carbonates when the sample is heated to the temperature $\theta_1$.

These carbonates are, for example but not exclusively, nahcolite (sodium bicarbonate $NaHCO_3$), dawsonite (double carbamate of sodium and aluminium ($NaAlCO_3$, $H_2O$) which are decomposed at temperatures comprised between 200° and 300° C., or also siderite (iron carbonate $FeCO_3$) whose decomposition temperature lies between 400° and 500° C., etc . . .

From the amount of hydrocarbons or hydrocarbon products is derived at 3, the amount $C_p$ of organic carbon contained in the effluents resulting from the pyrolysis of the sample in the inert atmosphere.

There is similarly evaluated at 4 the amount of mineral carbon $C_{m1}$ corresponding to the carbon dioxide produced by the early decomposition of some carbonates.

The values $C_p$ and $C_{m1}$ are recorded in the memories 5 and 6 respectively.

These determinations have been shown in solid line in FIG. 1.

The residue $E_R$ of the pyrolysis is an atmosphere of inert gas is placed into a heating chamber 7 which is preferably distinct from the heating chamber 1 for pratical reasons.

The residue $E_R$ is then heated in an oxidizing atmosphere ($O_2$ and/or air) to a temperature $\theta_2$ which is at most equal to the temperature $\theta_1$. In order that the measurements be achieved over a sufficiently short time interval, $\theta_2$ is an isotherm temperature fixed at the value $\theta_1 - \Delta\theta$ with:

$$0 < \Delta\theta < 50° \text{ C.}$$

Thus only the organic carbon contained in the sample residue $E_R$ produces carbon dioxide $CO_2$ which is transmitted through a valve 30 and analyzed at 8 and from which the corresponding amount of organic carbon $C_R$ is determined. The so-obtained information is transmitted to the memory 5 where the total amount of organic carbon "$C_{org}$ total" contained is this sample is imputed by adding the values $C_P$ and $C_R$.

Then, the temperature of the second heating chamber 7 is raised to a value $\theta_3$ capable of causing the decomposition of all the carbonated compounds contained in the sample and in particular those which decompose at a temperature higher than $\theta_1$.

The value $\theta_3$ of the temperature is thus, selected higher than $\theta_1$ and, for example, equal to 1000° C. thus providing for the decomposition of the carbonates, the main carbonates being calcite [$CaCO_3$], dolomite [$CaMg(CO_3)_2$] etc, whose thermal decomposition occurs above 600° C.

The carbon dioxide resulting from this decomposition of the carbonates is transmitted through the valve 30 to a device 9 which analyzes it and determines the corresponding amount $C_{m2}$ of mineral carbon.

This value is transmitted to the memory 6 where is added to the value $C_{m1}$ to give the total amount "$C_{min}$ Total" of mineral carbon contained in the analyzed sample.

Optionally, if so required, the total amount of carbon may be obtained by adding the values.

$$C_{org\ Total} + C_{min\ Total} = C_{Total}$$

The advantages of the present invention are apparent from the above description.

As a matter of fact, by accurately knowing the total amount of organic carbon it is possible to evaluate the oil production characteristics of the sediments from which the sample has been collected. It will be obviously possible to distinguish the hydrocarbons originally present in the sample from the hydrocarbons produced by cracking of the organic material in an inert atmosphere, by first heating the sample in the first chamber 1 to a temperature $\theta'_1$ of about 300° C. providing for vaporization of the hydrocarbons present in the sample without cracking the organic material. It is even possible to distinguish between gaseous and liquid hydrocarbons by first heating the sample to a temperature $\theta''_1$ generally lower than 90° C. which permits degassing of the gaseous hydrocarbons contained in the sample, then to the temperature $\theta'_1$ providing for the vaporization of the liquid hydrocarbons originally present in the sample and finally to the temperature $\theta_1$ comprised between 500° and 600° C. which provides for cracking of the organic material.

The amount of mineral carbon is also a valuable information for determining the lithology of the ground levels traversed by a borehole.

Figure 2:
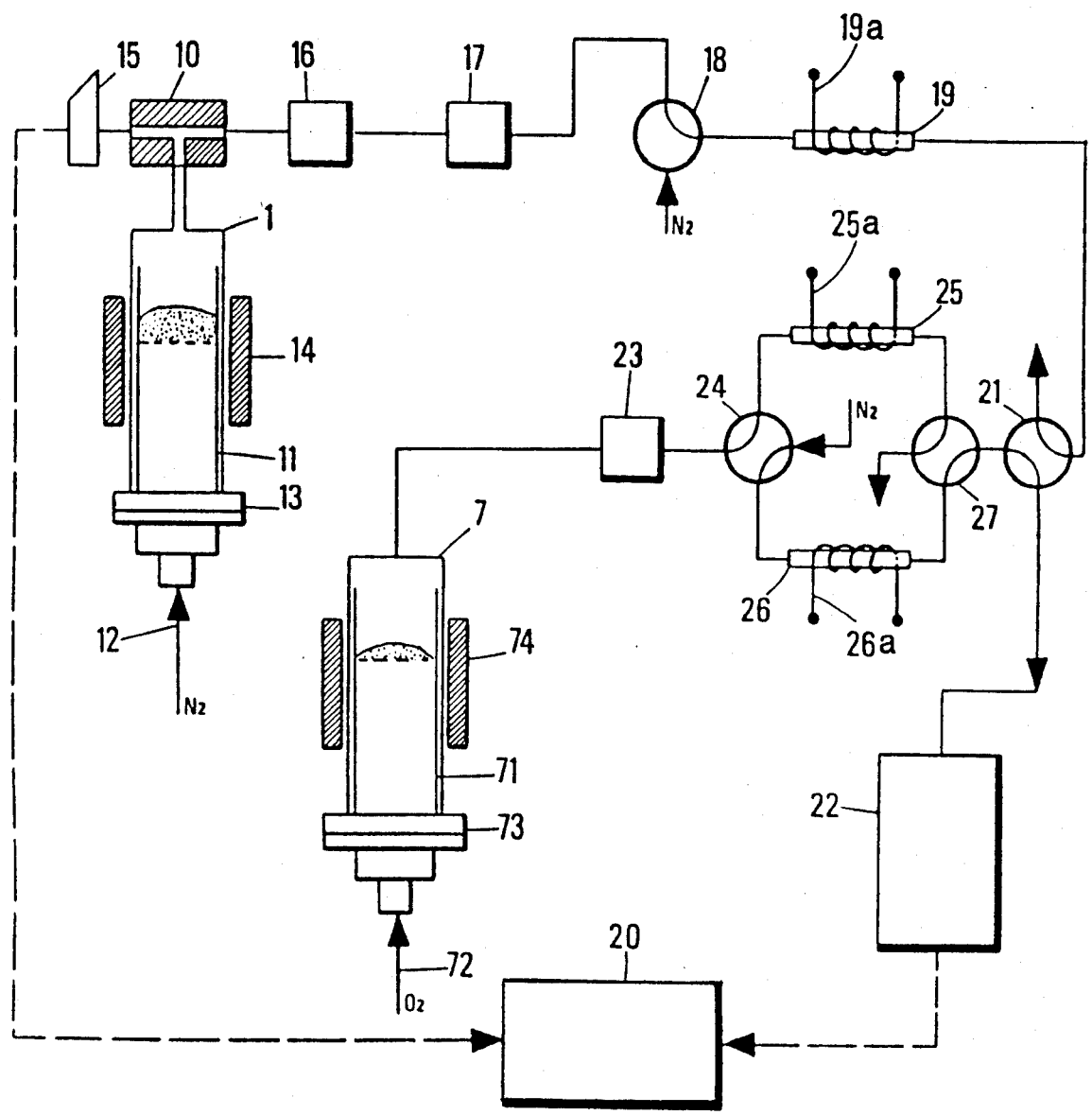
FIG. 2 diagrammatically shows an embodiment of the invention.

FIG. 2 diagrammatically shows an apparatus for carrying out the invention.

The apparatus comprises a first heating chamber 1, which in this embodiment is a sealed tubular housing preferably vertically positioned, into which a sample holder 11 can be introduced and which is fed with an inert gas such as nitrogen or helium through a pipe 12.

Displacement of the holder 11 and sealing are ensured by a device diagrammatically shown at 13. This heating chamber is equipped with means 14 which may be of any known type such as electrical resistor, etc ensuring temperature rise within the heating chamber 1 to a temperature $\theta_1$ comprised between 500° and 600° C., but these means may also be adapted to maintain in the chamber 1 a constant temperature $\theta_1$.

Means for controlling and programming the heating means may be provided. They have not been shown so as to not complicate the drawings but their realization only requires only ordinary skill.

At its upper part, the heating chamber 1 communicates with a flow dividing device 10 which is preferably at the same temperature as the chamber 1 to prevent condensation phenomena from occuring in the effluent resulting from the cracking of the organic material.

This flow divider provides for the transfer of a determined fraction of the effluent to a suitable detector 15, such as, for example, a flame ionization detector which delivers a signal representing the organic carbon content of the effluent. This signal is transmitted to a suitably processing circuit 20 which comprises a suitable programmed microprocessor.

The remaining fraction of the effluent produced by the cracking of the organic material in an inert atmosphere first flows through a hydrocarbon trap 16, then through a water trap 17, which respectively retain the hydrocarbons condensing at room temperature and water contained in the pyrolysis product. By means of a three-way, two-position valve 18 the effluent flows through a device 19 where carbon dioxide is trapped before the effluent is discharged to the atmosphere through a four-way, two-position valve 21.

At the end of the pyrolysis step in an inert atmosphere which is conducted over a period of at least five minutes, the valves 18 and 21 are actuated so as to connect the carbon dioxide trap 19 with a source of inert, gas such as helium, and with an apparatus 22 which is adapted to measure the amount of carbon dioxide received, and to determine the corresponding carbon content.

Simultaneously, the trap 19 is heated by heating means 19a to cause desorption of $CO_2$.

The measuring apparatus 22 delivers a signal representing the mineral carbon content which is derived from the amount of carbon dioxide resulting from the decomposition of carbonated products contained in the sample up to the temperature $\theta_1$.

The residue of the pyrolysis in an inert atmosphere is then transferred into a second heating chamber 7 of the same type as the chamber 1.

This furnace is comprised of a vertically positioned tubular housing into which a sample holder 71 can be introduced, this housing being fed with air and/or oxygen $O_2$ through a pipe 72. Displacement of the sample holder 71 and sealing are achieved by means diagrammatically indicated at 73.

This heating chamber 71 is provided with means 74 which may be of any known-type, such as an electric resistor, providing for the temperature rise within the heating chamber 7.

These heating means are adapted to maintain in the chamber 7 during a first time interval a temperature $\theta_2$ at most equal to the value $\theta_1$, and preferably differing from $\theta_1$ by a value $\Delta\theta$ comprised between 0 and 50° C. By way of example, good results have been obtained by selecting the following temperatures $\theta_1=600°$ C. and $\theta_2=550°$ C. These heating means are also adapted to maintain in the furnace 7 during a second step following the first step, a temperature $\theta_3$ comprised between 750° C. and 1100° C. and more generally, close to 1000° C.

Means for controlling and programming the heating device 74 can be provided but are not shown in the drawings.

At its upper part the heating chamber 7 communicates with a device 23 for trapping water and can be alternatively connected with the devices 25 and 26 through a four-way, two-position valves 24, the first of these devices trapping the carbon dioxide resulting from the oxidation of the organic material at the temperature $\theta_2$, while the second device traps the carbon dioxide produced by the decomposition at the temperature $\theta_3$ of the carbonated products still present in the sample. The carbon dioxide adsorbed by the devices 25 and 26 can be desorbed by heating (between 250°-350° C.) by means of heating elements 25a and 26a, to be separately transmitted to the measuring apparatus 22 through a four-way, two-position valve 27, and the valve 21.

The so-effected measurements are transmitted to the processing circuit 20 which then delivers the required informations, i.e. the total organic carbon and mineral carbon contents respectively.

To this end the processing circuit 20 may comprise a programmed micro-processor. This micro-processor may then be programmed to also automatically provide for the operation of the heating elements 14, 19a, 25a, 26a and 74, of the valves 18, 21, 24 and 27 and for the transfer of the sample from the chamber 1 to the chamber 7.

Figure 3:
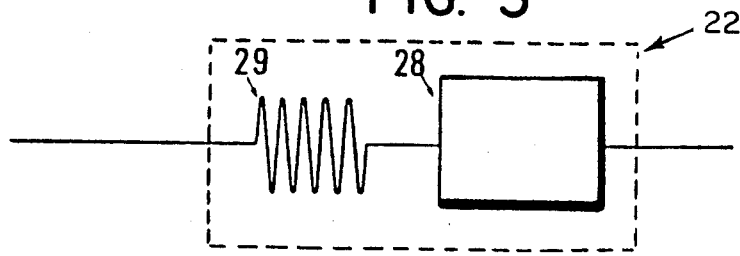
FIG. 3 schematically shows an embodiment of a device for determining the amount of carbon dioxide.

The carbon measuring apparatus 22 may be of any known type and may comprise a thermal conductivity detector or thermistor, or an infrared detector 28, etc, before which a chromatographic column 29 may optionally be located, as shown in FIG. 3.

Modifications may be made without departing from the scope of the invention.

For example, if only the total content of organic carbon is to be determined, only the corresponding steps of the method may be carried out.

What is claimed is:

1. A device for determining the total amount of organic carbon contained in a sample of sediment, comprising:
   first heating means for heating in an inert atmosphere, a sample to a first temperature wherein at least a fraction of carbon containing organic material is cracked therein;
   first measuring means for measuring only the amount of organic carbon contained in at least a fraction of effluents produced in said first heating means during cracking;
   second heating means for heating the sample in an oxidizing atmosphere to a second temperature at most equal to said first temperature wherein the residual organic material is oxidized;
   second measuring means separate from said first measuring means for measuring the amount of organic carbon contained in the effluent resulting from the oxidation of the organic carbon containing material heated in said second heating means; and
   processing means connected to said first and second measuring means for deriving the total organic carbon content of the sample from the measurements performed by said first and second measuring means.

2. A device for determining the quantity of organic carbon contained in a sample according to claim 1, wherein said first heating means comprises a first heating chamber equipped with means for raising the temperature of the sample to said first temperature value capable of cracking the organic material contained in the sample, a sample holder displaceable in said first heating chamber, first feed means for feeding said first heating chamber with an inert gas, said first heating chamber having first outlet means for discharging the effluents therefrom, said first measuring means comprising a first measuring element connected with said first outlet means and for delivering a first measuring signal ($C_p$) representative of the quantity of organic carbon contained in the effluents produced by cracking of the organic material in the inert atmosphere, said second heating means comprising a second heating chamber equipped with means for raising the temperature of the sample to said second temperature value at most equal to said first temperature value capable of oxidizing the residual organic material contained in the sample after cracking thereof in said first heating chamber, a sample holder displaceable in said second heating chamber, second feed means for feeding said second heating chamber with an oxidizing gas, said second chamber having second outlet means for discharging the effluents from said second chamber, said second measuring means comprising a second measuring element connected with said second outlet means and for delivering a second measuring signal ($C_R$) representative of the amount of residual organic carbon contained in the effluents produced by oxidation of the residual organic material in the oxidizing atmosphere in said second heating chamber, and means for processing said first ($C_P$) and second ($C_R$) measuring signals, said processing means deriving from said signals a resulting signal $C_P + C_R$ representative of the total quantity of organic material contained in the sample.

3. A device according to claim 2 for determining the total organic carbon and mineral carbon contents contained in a sample, wherein said first chamber heating means raises the temperature to said first value causing decomposition of all mineral carbonates decomposable up to said first temperature, said second chamber heating means for heating said second heating chamber having means for further raising the temperature to a third value for causing decomposition of all the remaining mineral carbonates contained in the sample, and wherein the device further comprises: (a) flow dividing means communicating with said first chamber for dividing into two fractions the effluents resulting from the cracking of the organic material in the inert atmosphere, a first of said two fractions being transmittable therethrough to said first measuring element that delivers said first signal $C_P$, the second of said two fractions being transmittable to said second measuring element that delivers a fourth signal $C_{m1}$ representative of all mineral carbonates decomposable up to said first temperature, (b) three circuits having means for temporarily adsorbing the carbon dioxide contained in the effluents flowed through said circuits, a first of said circuits communicating with said flow dividing means for receiving said second fraction of the effluents resulting from the cracking of the organic material in the inert atmosphere, (c) first connecting means for selectively and successively connecting said second heating chamber with the second and third circuits, so that the second circuit receives the effluents produced by heating of the residual organic material in an oxidizing atmosphere to the second temperature value, and the third circuit receives the effluents produced by heating the sample in an oxidizing atmosphere to the third temperature value causing decomposition of all the remaining mineral carbonates, (d) second connecting means for successively and selectively connecting said second and third circuits with said second measuring means, and (e) selector means for successively connecting each of the three circuits to said second measuring element which delivers the said second measuring signal $C_R$, said fourth measuring signal $C_{m1}$ and a third measuring signal $C_{m2}$ representative of all the remaining mineral carbonates decomposed up to said third temperature, and wherein said processing means for processing said signals from said first measuring element and said second measuring element derives from said first and second signals $C_P+C_R$ the total organic carbon and from said third and fourth signals $C_{m2}$ and $C_{m1}$ the mineral carbon content of the sample.

4. A device according to claim 3 further comprising a gas chromatographic column interposed between said selector means and second measuring element.

5. A device according to claim 3 wherein said processing means are programmed to control the operation of said connecting means, of said selector means and of both of said heating means, and to cause transfer of the sample from said first heating chamber to said second heating chamber.

6. A device according to claim 3 further comprising first trapping means for trapping hydrocarbons and water, with said first trapping means being interconnected between said first heating means and said selector means, and second trapping means for trapping water, with said second trapping means being interconnected between said second heating means and said selector means.

7. A device according to claim 3 further comprising third trapping and desorbing means for trapping and desorbing carbon dioxide from all the mineral carbonates decomposable up to said first temperature, said third trapping and desorbing means being interconnected between said first trapping means and said selector means, fourth trapping and desorbing means for trapping and desorbing carbon dioxide from all the residual organic material, said fourth trapping and desorbing means being interconnected between said first connecting means and said selector means, and fifth trapping and desorbing means for trapping and desorbing carbon dioxide from all the remaining mineral carbonates, said fifth trapping and desorbing means being interconnected between said first connecting means and said selector means.

8. A device according to claim 7 further comprising first valve means for selectively and successively connecting said first circuit to said third trapping means and for connecting said third trapping means with a source of inert gas, said first valve means being interconnected between said first and third trapping means, said first connecting means comprising second valve means, said second valve means for selectively and successively connecting said second heating chamber with said fourth and fifth trapping means and for connecting said fourth and fifth trapping means with a source of inert gas, said second valve means being interconnected between said second trapping means and said fourth and fifth trapping means, said second connecting means comprising third valve means, said third valve means for selectively and successively connecting said fourth and fifth trapping means to said second measuring element and for discharging the effluents to atmosphere, said third valve means being interconnected between said fourth and fifth trapping means and said second measuring means, and said selector means comprising fourth valve means, said fourth valve means for selectively and successively discharging the effluents from said first heating chamber to atmosphere and for connecting said third, fourth and fifth trapping means to said second measuring means, and said fourth valve means being interconnected between said second connecting means and said second measuring means.

* * * * *